(12) United States Patent
Janjic et al.

(10) Patent No.: US 6,762,290 B1
(45) Date of Patent: Jul. 13, 2004

(54) HIGH AFFINITY VASCULAR ENDOTHELIAL GROWTH FACTOR (VEGF) RECEPTOR NUCLEIC ACID LIGANDS AND INHIBITORS

(75) Inventors: Nebojsa Janjic, Boulder, CO (US); Larry Gold, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 09/364,540

(22) Filed: Jul. 29, 1999

(51) Int. Cl.$^7$ .......................... C12Q 1/68; C07H 21/04
(52) U.S. Cl. .......................... 536/23.1; 435/6
(58) Field of Search ............................ 536/23.1; 435/6

(56) References Cited

U.S. PATENT DOCUMENTS

| | | | |
|---|---|---|---|
| 5,459,015 A | 10/1995 | Janjic et al. |
| 5,659,013 A | 8/1997 | Senger et al. |
| 5,710,136 A | 1/1998 | Robinson et al. |
| 5,723,323 A | 3/1998 | Kauffman et al. |
| 5,811,533 A | 9/1998 | Gold et al. |
| 5,849,479 A | 12/1998 | Janjic et al. |
| 5,859,228 A | 1/1999 | Janjic et al. |
| 5,874,218 A | 2/1999 | Drolet et al. |

FOREIGN PATENT DOCUMENTS

| | | |
|---|---|---|
| GB | 2 183 661 A | 6/1987 |
| WO | WO89/06694 | 7/1989 |
| WO | WO 91/19813 | 12/1991 |
| WO | WO92/14843 | 9/1992 |
| WO | WO 94/10202 | 5/1994 |
| WO | WO 96/30046 | 10/1996 |
| WO | WO 97/09427 | 3/1997 |
| WO | WO 98/18480 | 5/1998 |

OTHER PUBLICATIONS

Rockwell, P. Cell–surface perturbations of the epidermal growth factor and vascular endothelial growth factor receptors by phosphorothioate oligodeoxynucleotides. Proc. Natl. Acad. Sci. USA. 1997, vol. 94, pp. 6523–6528.*
Wilson et al. Functional Requirements for Specific Ligands Recognition by a Biotin–Binding RNA Pseudoknot. Biochemistry. 1998, 37, 14410–14419.*
Ellington & Szostak (1990) Abstracts of papers presented at the 1990 meeting on RNA Processing, Cold Spring Harbor Laboratory, Cold Spring Harbor, NY, p. 84.
Joyce (1989) Gene 82:83.
Joyce & Inoue (1989) Nucleic Acids Research 17:711.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 344:467.
Szostak, "Structure and Activity of Ribozymes," in *Redesigning the Molecules of Life*, (S.A. Benner ed.) Springer–Verlag Berline Heidelberg, pp. 87–113 (1988).
Thiesen & Bach (1990) Nucleic Acids Research 18:3203.
De Vries et al. (1992) Science 255:989.
Galland et al. (1993) Oncogene 8:1233.
Gitay–Goren (1992) J. Biol. Chem. 267:6093.
Plate et al. (1992) Nature 359:845.
Vaisman et al. (1990) J. Biol. Chem. 265:19461.

* cited by examiner

Primary Examiner—Lorraine Spector
Assistant Examiner—Joseph F. Murphy
(74) Attorney, Agent, or Firm—Swanson & Bratschun, LLC

(57) ABSTRACT

Methods are described for the identification and preparation of high-affinity nucleic acid ligands to a VEGF receptor. Included in the invention are specific RNA ligands to a VEGF receptor identified by the SELEX method. Also included are RNA ligands that inhibit the interaction of a VEGF receptor with VEGF.

1 Claim, 1 Drawing Sheet

SEQUENCE LISTING

<160> NUMBER OF SEQ ID NOS: 36

<210> SEQ ID NO 1
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F; N at positions 16 - 55 is any base.
<220> FEATURE:
<223> OTHER INFORMATION: Description of Artificial Sequence: Synthetic Sequence

<400> SEQUENCE: 1
gggaggacga ugcggnnnnn nnnnnnnnnn nnnnnnnnnn nnnnnnnnnn nnnnncagac    60
gacucgcccg a                                                          71

<210> SEQ ID NO 2
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 2
gggaggacga ugcggcaugg ggccugacug gaucauacca ccgcuuucuc ggucagacg      60 acucgcccga                                                            70

<210> SEQ ID NO 3
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 3
gggaggacga ugcggcaugg ggccugacug gaucauacca ccgcuuccuc ggucagacg      60 acucgcccga                                                            70

<210> SEQ ID NO 4
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 4
gggaggacga ugcggcaugg ggccugacug gaucauacca ccgcuuccuc ugggucagac     60
gacucgcccg a                                                          71

<210> SEQ ID NO 5
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 5
gggaggacga ugcggccugg ggccugacug gaucauacca ccgcuuccuc ugggucagac     60
gacucgcccg a                                                          71

<210> SEQ ID NO 6
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
    Sequence

<400> SEQUENCE: 6
gggaggacga ugcggacgau aacacagggc cugcuuggau cacacugauu gcgcccagac    60
gacucgcccg a                                                        71

<210> SEQ ID NO 7
<211> LENGTH: 72
<212> TYPE: RNA
<213> ORGANISM: Artificial Sequence
<220> FEATURE:
<221> NAME/KEY: modified_base
<222> LOCATION: (1)..(72)
<223> OTHER INFORMATION: All pyrimidines are 2'F; n at position 19 is
    any base.
<220> FEATURE:
<223> OTHER INFORMATION: Description of Artificial Sequence: Synthetic
    Sequence

<400> SEQUENCE: 7
gggaggacga ugcggacana uaacacaggg ccugcuugga ucacacugau ugcgcccaga    60
cgacucgccc ga                                                       72

<210> SEQ ID NO 8
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence: Synthetic
    Sequence

<400> SEQUENCE: 8
gggaggacga ugcggcgaua acacagggcc ugcuuggauc acacugauug cgcccagacg    60
acucgcccga                                                          70

<210> SEQ ID NO 9
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
    Sequence

<400> SEQUENCE: 9
gggaggacga ugcggacgau aacacagggc cugcuuggau cacacugauu gcgcccagac    60
gacucgcccg a                                                        71

<210> SEQ ID NO 10
<211> LENGTH: 71

```
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 10
gggaggacga ugcggggccu guuuggauca uaccgaucgu caauccaaga guggucagac       60
gacucgcccg a                                                            71

<210> SEQ ID NO 11
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 11
gggaggacga ugcggggccu guuuggauca uaccgaucgu caauccuaaa guggucagac       60
gacucgcccg a                                                            71

<210> SEQ ID NO 12
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 12
gggaggacga ugcggggccu gcuuggauca uaccgaucgu caauccuaaa guggucagac       60
gacucgcccg a                                                            71

<210> SEQ ID NO 13
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 13
gggaggacga ugcggggccu gcuuggauca uaccgaucgu caagccuaaa guggucagac       60
gacucgcccg a                                                            71

<210> SEQ ID NO 14
<211> LENGTH: 70
<212> TYPE: RNA
<213> ORGANISM: Artificial Sequence
<220> FEATURE:
```

```
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 14
gggaggacga ugcggucuga agaguaaggg gccuguucgg aucacaccug ccgucagacg    60
acucgcccga                                                           70

<210> SEQ ID NO 15
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 15
gggaggacga ugcggagggc cuauucggau cauacucgca guucuuuuac cccgucagac    60
gacucgcccg a                                                         71

<210> SEQ ID NO 16
<211> LENGTH: 69
<212> TYPE: RNA
<213> ORGANISM: Artificial Sequence
<220> FEATURE:
<221> NAME/KEY: modified_base
<222> LOCATION: (1)..(69)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 16
gggaggacga ugcggagggc cuauucggau cauacucgca guucuuaccc cgucagacga    60
cucgcccga                                                            69

<210> SEQ ID NO 17
<211> LENGTH: 69
<212> TYPE: RNA
<213> ORGANISM: Artificial Sequence
<220> FEATURE:
<221> NAME/KEY: modified_base
<222> LOCATION: (1)..(69)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 17
gggaggacga ugcgggggcc uaacuuggau caucagcacc ugccaccacc ccucagacga    60
cucgcccga                                                            69

<210> SEQ ID NO 18
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
```

```
<220> FEATURE:
<223> OTHER INFORMATION: Description of Artificial Sequence:  Synthetic
      Sequence

<400> SEQUENCE: 18
gggaggacga ugcggaggug cuccuuugga acuucguauu ugucugcucc cggucagacg      60
acucgcccga                                                            70

<210> SEQ ID NO 19
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence:  Synthetic
      Sequence

<400> SEQUENCE: 19
gggaggacga ugcggaucau accgaagaga cacggggcca ccauauccuc accccagac      60 gacucgcccg a                                                          71

<210> SEQ ID NO 20
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F; n at positions 38 and
      51 is any base.
<220> FEATURE:
<223> OTHER INFORMATION: Description of Artificial Sequence:  Synthetic
      Sequence

<400> SEQUENCE: 20
gggaggacga ugcggaucau accgggucau aacaccgnuc acggggccuu nucgucagac      60
gacucgcccg a                                                          71

<210> SEQ ID NO 21
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence:  Synthetic
      Sequence

<400> SEQUENCE: 21
gggaggacga ugcggaggug cuccuuugga acuucguauu ugucugcucc uggucagacg      60
acucgcccga                                                            70

<210> SEQ ID NO 22
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence:  Synthetic
```

Sequence

<400> SEQUENCE: 22
gggaggacga ugcgguugau cgagguucua aggccuauuu ccugacuuuc uccccagac      60 gacucgcccg a                                                          71

<210> SEQ ID NO 23
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 23
gggaggacga ugcgguugau cgagguucua aagccuauuu ccugacuuuc uccccagac      60 gacucgcccg a                                                          71

<210> SEQ ID NO 24
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 24
gggaggacga ugcggaaacg gaagaauugg agaccgacgu cgaccucuug gccccagacg      60
acucgcccga                                                            70

<210> SEQ ID NO 25
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 25
gggaggacga ugcgguugau cgagguucua aagccuauuu cugacuuucu ccccagacg      60 acucgcccga                                                            70

<210> SEQ ID NO 26
<211> LENGTH: 70
<212> TYPE: RNA
<213> ORGANISM: Artificial Sequence
<220> FEATURE:
<221> NAME/KEY: modified_base
<222> LOCATION: (1)..(70)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 26
gggaggacga ugcggacgau gcggaaucag ugaaugcuua uagcuccgcc uggucagacg    60
acucgcccga                                                          70

<210> SEQ ID NO 27
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 27
gggaggacga ugcggaagcc gccagaauug gaacaacccc uuucgcacgc uccccagac    60 gacucgcccg a                                                        71

<210> SEQ ID NO 28
<211> LENGTH: 71
<212> TYPE: RNA
<213> ORGANISM: Artificial Sequence
<220> FEATURE:
<221> NAME/KEY: modified_base
<222> LOCATION: (1)..(71)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 28
gggaggacga ugcggcgaaa cggaauacuu ggauacaccg cacucccga ccccucagac    60 gacucgcccg a                                                        71

<210> SEQ ID NO 29
<211> LENGTH: 61
<212> TYPE: RNA
<213> ORGANISM: Artificial Sequence
<220> FEATURE:
<221> NAME/KEY: modified_base
<222> LOCATION: (1)..(61)
<223> OTHER INFORMATION: All pyrimidines are 2'F; n at position 30 is
      any base.
<220> FEATURE:
<223> OTHER INFORMATION: Description of Artificial Sequence: Synthetic
      Sequence

<400> SEQUENCE: 29
gggaggacga ugcggagcac uugacccacn accagaaagc cagcccagac gacucgcccg    60
a                                                                   61

<210> SEQ ID NO 30
<211> LENGTH: 61
<212> TYPE: RNA
<213> ORGANISM: Artificial Sequence
<220> FEATURE:
<221> NAME/KEY: modified_base
<222> LOCATION: (1)..(61)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 30
gggaggacga ugcggaacca auuaagucug gcaaaucucu cugugcagac gacucgcccg    60
a                                                              61

<210> SEQ ID NO 31
<211> LENGTH: 61
<212> TYPE: RNA
<213> ORGANISM: Artificial Sequence
<220> FEATURE:
<221> NAME/KEY: modified_base
<222> LOCATION: (1)..(61)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 31
gggaggacga ugcggacaca cacaucauaa acauuguccg uugaccagac gacucgcccg    60
a                                                              61

<210> SEQ ID NO 32
<211> LENGTH: 64
<212> TYPE: RNA
<213> ORGANISM: Artificial Sequence
<220> FEATURE:
<221> NAME/KEY: modified_base
<222> LOCATION: (1)..(64)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 32
gggaggacga ugcgggcggc augggccug acuggaucau accaccgcca gacgacucgc    60
ccga                                                           64

<210> SEQ ID NO 33
<211> LENGTH: 63
<212> TYPE: RNA
<213> ORGANISM: Artificial Sequence
<220> FEATURE:
<221> NAME/KEY: modified_base
<222> LOCATION: (1)..(63)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 33
gggaggacga ugcgguaaca cagggccugc uuggaucaca cugauugcag acgacucgcc    60
cga                                                            63

<210> SEQ ID NO 34
<211> LENGTH: 67
<212> TYPE: RNA
<213> ORGANISM: Artificial Sequence
<220> FEATURE:
<221> NAME/KEY: modified_base
<222> LOCATION: (1)..(67)
<223> OTHER INFORMATION: All pyrimidines are 2'F.
<220> FEATURE:
<223> OTHER INFORMATION: Description of Artificial Sequence: Synthetic
      Sequence

<400> SEQUENCE: 34
gggaggacga ugcgggacga ugcggggccu guuuggauca uaccgaucgu ccagacgacu    60
cgcccga                                                        67

```
<210> SEQ ID NO 35
<211> LENGTH: 59
<212> TYPE: RNA
<213> ORGANISM: Artificial Sequence
<220> FEATURE:
<221> NAME/KEY: modified_base
<222> LOCATION: (1)..(59)
<223> OTHER INFORMATION: All pyrimidines are 2'F.
<220> FEATURE:
<223> OTHER INFORMATION: Description of Artificial Sequence:  Synthetic
      Sequence

<400> SEQUENCE: 35
gggaggacga ugcggcggau cauaccgaag agacacgggg ccacagacga cucgcccga         59

<210> SEQ ID NO 36
<211> LENGTH: 68
<212> TYPE: RNA
<213> ORGANISM: Artificial Sequence
<220> FEATURE:
<221> NAME/KEY: modified_base
<222> LOCATION: (1)..(68)
<223> OTHER INFORMATION: All pyrimidines are 2'F; n at position 41 is
      any base.
<220> FEATURE:
<223> OTHER INFORMATION: Description of Artificial Sequence:  Synthetic
      Sequence

<400> SEQUENCE: 36
gggaggacga ugcggcggau cauaccgggu cauaacaccg nucacggggc cucagacgac         60
ucgcccga                                                                 68
```

HIGH AFFINITY VASCULAR ENDOTHELIAL GROWTH FACTOR (VEGF) RECEPTOR NUCLEIC ACID LIGANDS AND INHIBITORS

FIELD OF THE INVENTION

Described herein are methods for identifying and preparing high affinity nucleic acid ligands that bind to a VEGF receptor. The method utilized herein for identifying such nucleic acid ligands is called SELEX, an acronym for Systematic Evolution of Ligands by EXponential Enrichment. This invention includes high affinity nucleic acids to a VEGF receptor. Further disclosed are RNA ligands to a VEGF receptor. Also included are oligonucleotides containing nucleotide derivatives modified at the 2' position of the pyrimidines. Additionally disclosed are ligands to a VEGF receptor containing 2'-F modifications of the pyrimidines. This invention also includes high affinity nucleic acid inhibitors of VEGF signaling. The oligonucleotide ligands of the present invention are useful in any process in which binding of VEGF to a VEGF receptor is required. This includes, but is not limited to, their use as pharmaceuticals, diagnostics, imaging agents, and immunohistochemical reagents.

BACKGROUND OF THE INVENTION

Angiogenesis in Disease

The growth of new blood vessels from existing endothelium (angiogenesis) is tightly controlled in healthy adults by opposing effects of positive and negative regulators. Under certain pathological conditions, including proliferative retinopathies, rheumatoid arthritis, psoriasis and cancer, positive regulators prevail and angiogenesis contributes to disease progression (reviewed in Folkman (1995) Nature Med. 1:27–31). In cancer, the notion that angiogenesis represents the rate limiting step of tumor growth and metastasis (Folkman (1971) New Engl. J. Med. 285:1182–1186) is now supported by considerable experimental evidence (reviewed in Aznavoorian et al. (1993) Cancer 71:1368–1383; Fidler and Ellis (1994) Cell 79:185–188; Folkman (1990) J. Natl. Cancer Inst. 82:4–6). The quantity of blood vessels in tumor tissue is a strong negative prognostic indicator in breast cancer (Weidner et al. (1992) J. Natl. Cancer Inst. 84:1875–1887), prostate cancer (Weidner et al. (1993) Am. J. Pathol. 143:401–409), brain tumors (Li et al.(1994) Lancet 344:82–86), and melanoma (Foss et al.(1996) Cancer Res. 56:2900–2903).

VEGF Signaling in Angiogenesis

A number of angiogenic growth factors have been described to date among which vascular endothelial growth factor (VEGF) appears to play a key role as a positive regulator of physiological and pathological angiogenesis (reviewed in Brown et al. (1997) in Control of Angiogenesis (Goldberg and Rosen, eds.), Birkhauser, Basel: 233–269; Thomas (1996) J. Biol. Chem. 271:603–606; Neufeld et al. (1999) FASEB J. 13: 9–22). VEGF is a secreted disulfide-linked homodimer that selectively stimulates endothelial cells to proliferate, migrate, and produce matrix-degrading enzymes (Conn et al. (1990) Proc. Natl. Acad. Sci. U.S.A. 87: 1323–1327; Ferrara and Henzel (1989) Biochem. Biophys. Res. Commun. 161: 851–858; Gospodarowicz et al. (1989) Proc. Natl. Acad. Sci. U.S.A. 86: 7311–7315; Pepper et al. (1991) Biochem. Biophys. Res. Commun. 181: 902–906; Unemori et al. (1992) J. Cell. Physiol. 153: 557–562), all of which are processes required for the formation of new vessels. In addition to being the only known endothelial cell specific mitogen, VEGF is unique among angiogenic growth factors in its ability to induce a transient increase in blood vessel permeability to macromolecules (hence its original and alternative name, vascular permeability factor) (Dvorak et al.(1979) J. Immunol. 122:166–174; Senger et al.(1983) Science 219:983–985; Senger et al.(1986) Cancer Res. 46:5629–5632). Increased vascular permeability and the resulting deposition of plasma proteins in the extravascular space assists the new vessel formation by providing a provisional matrix for the migration of endothelial cells (Dvorak et al.(1995) Am. J. Pathol. 146:1029–1039). Hyperpermeability is indeed a characteristic feature of new vessels, including those associated with tumors (Dvorak et al.(1995) Am. J. Pathol. 146:1029–1039). Furthermore, compensatory angiogenesis induced by tissue hypoxia is now known to be mediated by VEGF (Levy et al.(1996) J. Biol. Chem. 271:2746–2753); Shweiki et al. (1992) Nature 359:843–845).

VEGF is produced and secreted in varying amounts by virtually all tumor cells (Brown et al. (1997) in Control of Angiogenesis, ibid). Direct evidence that VEGF and its receptors contribute to tumor growth was recently obtained by a demonstration that the growth of human tumor xenografts in nude mice could be inhibited by neutralizing antibodies to VEGF (Kim et al. (1993) Nature 362:841–844), by the expression of dominant-negative VEGFR2 (Millauer et al. (1996) Cancer Res. 56:1615–1620; Millauer et al. (1994) Nature 367:576–579), by low molecular weight inhibitors of VEGF receptor inhibitors (Strawn et al. (1966) Cancer Res. 56:3540–3545), or by the expression of antisense sequence to VEGF mRNA (Saleh et al. (1996) Cancer Res. 56:393401). Importantly, the incidence of tumor metastases was also found to be dramatically reduced by VEGF antagonists (Asano et al. (1995) Cancer Res. 55, 5296–5301; Warren et al. (1995) J. Clin. Invest. 95: 1789–1797; Claffey et al. (1996) Cancer Res. 56:172–181; Melnyk et al. (1996) Cancer Res. 56, 921–924). Inhibitors of VEGF signaling may thus have broad clinical utility as anticancer agents. In addition to cancer, as noted above, other proliferative diseases characterized by excessive neovascularization such as psoriasis, age-related macular degeneration, diabetic retinopathy and rheumatoid arthritis could be treated with antagonists of VEGF signaling.

VEGF occurs in several forms (VEGF-121, VEGF-145, VEGF-165, VEGF-189, VEGF-206) as a result of alternative splicing of the VEGF gene that consists of eight exons (Houck et al. (1991) Mol. Endocrin. 5:1806–1814; Tischer et al. (1991) J. Biol. Chem. 266:11947–11954; Poltorak et al. (1997) J. Biol. Chem. 272: 7151–7158). The three smaller forms are diffusable while the larger two forms remain predominantly localized to the cell membrane as a consequence of their high affinity for heparin. VEGF-165 and VEGF-145 also bind to heparin (as a consequence of containing basic exon 7- and exon 6-encoded domains, respectively), albeit with somewhat lower affinity compared with VEGF-189 (that contains both exons 6 and 7). VEGF-165 appears to be the most abundant form in most tissues (Houck et al. (1991) Mol. Endocrinol., ibid; Carmeliet et al. (1999) Nature Med. 5: 495–502). VEGF-121, the only alternatively spliced form that does not bind to heparin, appears to have a somewhat lower affinity for the receptors (Gitay-Goren et al. (1996) J. Biol. Chem. 271:5519–5523) as well as lower mitogenic potency (Keyt et al. (1996) J. Biol. Chem. 271:7788–7795).

VEGF Receptors

Biological effects of VEGF are mediated by two homologous tyrosine kinase receptors, Flt-1 (VEGFR1) and Flk-1/KDR (VEGFR2) whose expression is highly restricted to cells of endothelial origin (de Vries et al. (1992) Science 255: 989–991; Millauer et al. (1993) Cell 72: 835–846; Terman et al. (1991) Oncogene 6: 519–524). Both receptors have an extracellular domain consisting of seven IgG-like domains, a transmembrane domain and an intracellular tyrosine kinase domain. The affinity of VEGFR1 for VEGF ($K_d$=1–20 pM) is higher compared to that of VEGFR2

($K_d$=50–770 pM) (Brown et al. (1997) in Regulation of Angiogenesis, ibid; de Vries et al. (1992) Science 255, 989–991; Terman et al. (1992) Biochem. Biophys. Res. Commun. 187, 1579–1586). In human umbilical cord endothelial cells (HUVECs) in 2-dimensional culture, VEGFR2 is by far the more abundant receptor (Brown et al. (1997) in Regulation of Angiogenesis, ibid). In vivo, however, in quiescent endothelial cells, both receptors are expressed at low levels (Kremer et al. (1997) Cancer Res. 57, 3852–3859; Barleon et al. (1997) Cancer Res. 57: 5421–5425).

Both receptors are substantially upregulated when endothelial cells are activated by a variety of stimuli. Hypoxia, for example, induces an increase in expression of both VEGFR1 and VEGFR2 in endothelial cells (Tuder et al. (1995) J. Clin. Invest. 95: 1798–1807; Gerber et al. (1997) J. Biol. Chem. 272: 23659–23667; Brogi et al. (1996) J. Clin. Invest. 97: 469–476; Kremer et al. (1997) Cancer Res., ibid). For VEGFR 1, hypoxia leads to both direct activation via the flt-1 promoter that contains the hypoxia-inducible-factor-1 (HIF-1) consensus binding site (Gerber et al. (1997) J. Biol. Chem., ibid) and indirect activation via hypoxia-induced VEGF (Barleon et al. (1997) Cancer Res., ibid). VEGF-induced upregulation of VEGFR1 is mediated by both VEGFR1 and VEGFR2 (Barleon et al. (1997) Cancer Res., ibid). VEGFR2 is upregulated by VEGF (through VEGFR2 but not VEGFR1) (Kremer et al. (1997) Cancer Res., ibid; Wilting et al. (1996) Dev. Biol. 176:76–85) and possibly by a yet unidentified factor in hypoxia-conditioned media from myoblasts (Brogi et al. (1996) J. Clin. Invest., ibid). The expression of VEGFR2 in endothelial cells is also upregulated by bFGF and this accounts in part for the synergistic activation of endothelial cells by VEGF and bFGF (Pepper et al. (1998) Exp. Cell Res. 241, 414–425). In addition, since both kdr and flt-1 promoters contain a cis-acting fluid shear-stress-responsive element, VEGFR1 and VEGFR2 expression may be sensitive to variations in blood flow (Tuder et al. (1995) J. Clin. Invest., ibid).

Experiments using porcine aortic endothelial (PAE) cells transfected with the flt-1 or kdr receptor genes have suggested that VEGFR2 is the primary transducer in endothelial cells of VEGF-mediated signals related to changes in cell morphology and mitogenicity (Waltenberger et al. (1994) J. Biol. Chem. 269, 26988–26995). In the same study, stimulation of flt-1-transfected PAE cells with VEGF did not appear to produce detectable changes. More recently, however, it was demonstrated that VEGF signaling through VEGFR1 induces migration of monocytes and upregulation of tissue factor expression in both endothelial cells and monocytes (Clauss et al. (1996) J. Biol. Chem. 271, 17629–17634; Barleon et al. (1996) Blood 87, 3336–3343). Based on the observation that the extracellular domain of VEGFR2 is retained on a cation exchange resin only in the presence of VEGFR1 and that the VEGFR2 retention is enhanced when both VEGFR1 and VEGF were present, Kendall et al. have concluded that the two receptors have some affinity for one another and that this interaction is stabilized by VEGF (Kendall et al. (1996) Biochem Biophys. Res. Commun. 226, 324–328). When both receptors are expressed on cell surface, it appears likely that the VEGFR1/R2 heterodimer constitutes at least a fraction of the binding-competent VEGF receptor.

Gene Deletion Studies of VEGF and VEGF Receptors

The functions of VEGFR1 and VEGFR2 have further been elucidated by targeted gene deletion studies. While deletion of either VEGFR1 or VEGFR2 results in embryonic lethality as a result of vascular abnormalities, there are important differences in the two phenotypes.

In mice deficient in VEGFR1, endothelial cells are formed but organize into distended and dilated vessels (Fong et al. (1995) Nature 376: 66–70). Interestingly, mice that only lack the tyrosine kinase domain of VEGFR1 (and thus display the receptor on cell surfaces that is incapable of signaling) are viable, with the only detectable abnormality being the strongly suppressed macrophage migration in response to VEGF (Hiratsuka et al. (1998) Proc. Natl. Acad. Sci. 95: 9349–9354). Since vascular abnormalities of VEGFR1 knockout mice are similar to those observed in transgenic mice that overexpress VEGF during development, it has been suggested that VEGFR1 is primarily a negative regulator of VEGF signaling, and that partial inhibition of VEGF signaling is essential for proper vessel development (Hiratsuka et al. (1998) Proc. Natl. Acad. Sci., ibid). It is relevant to note in this context that VEGFR1 also exists as an alternatively spliced secreted extracellular domain that acts as a potent inhibitor of VEGF (Kendall et al. (1993) Proc. Natl. Acad. Sci., U.S.A. 90: 10705–10709). The importance of tightly controlled VEGF signaling during development is further evidenced by the lethal phenotype of mice that lack only one allele of the VEGF gene (Carmeliet et al. (1996) Nature 380:435–439; Ferrara et al. (1996) Nature 380:439–442) and also of mice that only express the smallest isoform of VEGF (VEGF-120) (Carmeliet et al. (1999) Nature Med. 5, 495–502). Thus, deviations on either side from a precisely determined level of VEGF signaling results in embryonic lethality.

Mice deficient in VEGFR2 lack both endothelial cells and hematopoietic cells, a more severe phenotype compared to that of VEGFR1 knockout, that results in embryonic lethality at day 8 (Shalaby et al. (1995) Nature 376:62–66). This is presumably a consequence of the fact that these two cell types arise from a common, VEGFR2-expressing precursor, the hemangioblast (Eichmann et al. (1997) Proc. Natl. Acad. Sci. 94: 5141–5146).

Structural Requirements for Binding

Crystal structure of the receptor-binding domain of VEGF (residues 8–109) has recently been reported (Muller et al. (1997) Proc. Natl. Acad. Sci., U.S.A. 94: 7192–7197; Muller et al. (1997) Structure 5:1325–1338). In the VEGF homodimer, the monomers are oriented in an antiparallel manner with two intersubunit disulfide bonds being formed between Cys51 from one subunit and Cys60 from the other. The three intrasubunit disulfide bonds are clustered in a characteristic cysteine knot motif (Sun et al. (1995) Annu. Rev. Biophys. Biomol. Struct. 24: 269–291) also observed in PDGF and TGFβ2. Despite low sequence homology (about 20%), PDGF and VEGF have very similar structures. Both proteins have an elongated shape in which each of the subunits consist primarily of four antiparallel β strands connected with three solvent accessible loops. In the homodimer, loops I and III from one subunit are adjacent to loop II from the other subunit. Alanine-scanning mutagenesis studies of VEGF have identified discrete regions that are important for high affinity binding to VEGFR1 and VEGFR2 (Keyt et al. (1996) J. Biol. Chem. 271, 5638–5646; Muller et al. (1997) Proc. Natl. Acad. Sci., U.S.A. 94, 7192–7197). Amino acid residues most critical for binding of VEGF to VEGFR1 are D63 and E64 in loop II. Residues most critical for binding of VEGF to VEGFR2 are R82-H86 encompassing loop III, I46 in loop I and E64 in loop II. Knowledge of the importance of these regions for receptor binding has been utilized to generate VEGF mutants in which only one side of the VEGF homodimer was rendered defective for receptor binding (Siemeister et al. (1998) Proc. Natl. Acad. Sci., U.S.A. 95: 4625–4629; Fuh et al. (1998) J. Biol. Chem. 273: 11197–11204). As expected, such monovalent VEGF mutants are inhibitors of VEGF-induced signaling since they are deficient in their ability to dimerize the receptors. Interestingly, avidity effects play a greater role in the binding of VEGF to VEGFR2 than to VEGFR1. The affinity of monomeric VEGFR1 for wild-type VEGF dimer is reduced only about 2-fold compared to that of dimeric VEGFR 1 (IgG fusion construct) (Weismann et al. (1997)

Cell 91, 695–704). In contrast, the affinity of monomeric VEGFR2 for VEGF is reduced 100-fold compared to the dimeric VEGFR2 (Fuh et al. (1998) J. Biol. Chem., ibid). Comparing only the monomeric forms, VEGFR1 binds to VEGF with about 100-fold higher affinity compared to VEGFR2.

Domain deletion studies of the extracellular region of the VEGF receptors have shown that out of seven IgG-like domains, domains 2 and 3 of VEGFR1 (Davis-Smyth et al. (1996) EMBO J. 15: 4919–4927; Barleon et al. (1997) J. Biol. Chem. 272: 10382–10388) and VEGFR2 (Fuh et al. (1998) J. Biol. Chem. 273, 11197–11204; Shinkai et al. (1998) J. Biol. Chem. 273, 31283–31288) are essential for VEGF binding. Crystal structure of the complex between $VEGF_{8-109}$ with IgG domain 2 of VEGFR1 (that bind to VEGF with only 60-fold reduced affinity compared to the entire extracellular domain of the receptor) shows the receptor to be in contact with both subunits of $VEGF_{8-109}$ in an interaction dominated by hydrophobic contacts (Weismann et al. (1997) Cell, ibid).

VEGF-165 Receptors

In addition to VEGFR1 and VEGFR2, receptors that only bind VEGF-165 and not VEGF-121 have been identified on endothelial cells and some tumor cells (Soker et al. (1996) J. Biol. Chem. 271: 5761–5767; Soker et al. (1997) J. Biol. Chem. 272: 31582–31588; Omura et al. (1997) J. Biol. Chem. 272: 23317–23322). One such receptor unrelated in sequence to the tyrosine kinase receptors and with a short cytoplasmic domain, neuropilin-1, is also a receptor for semaphorins which play a role in neuronal chemorepulsion during development (Soker et al. (1998) Cell 92:735–745). Since the binding of VEGF-165 to neuropilin-1 involves the exon 7-encoded domain that is not required for the binding to VEGFR1 and VEGFR2, it has been suggested that neuropilin-1 serves as a co-receptor for VEGF-165. The presence of such receptors on endothelial cells may in part account for the enhanced mitogenic activity of VEGF-165 compared to VEGF-121. Consistent with this notion is the observation that cardiovascular system of neuropilin-1 knockout mice does not develop normally leading to embryonic lethality (Kitsukawa et al. (1997) Neuron 19: 995–1005). The questions of what role VEGF may play in neuronal development and conversely, whether semaphorins have a role in vascular development and function, remain to be answered.

Receptor Binding Specificity of Various Forms of VEGF and Other Proteins in the VEGF Family In addition to the alternatively spliced forms of VEGF, additional species can be generated by proteolytic processing. Plasmin cleaves VEGF-165 and VEGF-189 between residues Arg-110 and Ala-111 to generate VEGF-110 as the amino terminus fragment (Keyt et al. (1996) J. Biol. Chem., ibid; Plouët et al. (1997) J. Biol. Chem 272: 13390–13396). Since it contains the receptor binding domain (supra), VEGF-110 bind to both VEGFR1 and VEGFR2. Like VEGF-121, VEGF-110 does not bind to heparin and its potency is lower compared to that of VEGF-165 (Keyt et al. (1996) J. Biol. Chem., ibid). Interestingly, VEGF-189 can bind to VEGFR1 but not VEGFR2 and this renders it inactive as an endothelial cell mitogen (Houck et al. (1991) Mol. Endocrinol., ibid; Plouët et al. (1997) J. Biol. Chem. 272, ibid). VEGF-189 thus requires proteolytic processing either by plasmin or by urokinase-type plasminogen activator (that cleaves VEGF-189 in the exon 6encoded domain to generate a 40 kDa fragment) to gain ability to bind to VEGFR2 (Plouët et al. (1997) J. Biol. Chem., ibid).

Proteins with sequence homology to VEGF (also referred to as VEGF-A) have recently been described including placenta growth factor (PlGF: Park et al. (1994) J. Biol. Chem. 269: 25646–25654), VEGF-B (Olofsson et al. (1996) Proc. Natl. Acad. Sci., U.S.A. 93: 2576–2581), VEGF-C (Lee et al. (1996) Proc. Natl. Acad. Sci., U. S. A. 93:1988–1992; Joukov et al. (1996) EMBO J. 15: 290–298), VEGF-D (Achen et al. (1998) Proc. Natl. Acad. Sci., U.S.A. 95: 548–553) and VEGF-E (Ogawa et al. (1998) J. Biol. Chem. 273: 31273–31282). In terms of receptor binding specificity, PlGF and VEGF-B can bind only to VEGFR1 with high affinity. VEGF-C and VEGF-D bind to VEGFR2 and another related tyrosine kinase, Flt-4 or VEGFR3. The expression of VEGFR3 appears to be confined to lymphatic endothelial cells. VEGF-E, a protein encoded in the genome of the Orf virus, binds only to VEGFR2 (Ogawa et al. (1998) J. Biol. Chem. 273: 31273–31282). Some of these proteins including PlGF and VEGF-B can form heterodimers with VEGF (Cao et al. (1996) J. Biol. Chem. 271: 3154–3162; DiSalvo et al. (1996) J. Biol. Chem. 270: 7717–7723). The function of these VEGF-related molecules in physiological and pathological conditions remains to be precisely defined, however, it is clear that some redundancy of signaling mediated by VEGF receptors exists (Nicosia (1998) Am. J. Pathol. 153: 11–16).

VEGF Receptors on Non-endothelial Cells

Although VEGFR1 and VEGFR2 are expressed predominantly on endothelial cells, they have also been detected on some non-endothelial cells. VEGFR1 is expressed on trophoblasts (Charnockjones et al. (1994) Biol. Reprod. 51: 524–530), monocytes (Barleon et al. (1996) Blood, ibid), hematopoietic stem cells and megakaryocytes/platelets (Katoh et al. Cancer Res. 55: 5687–5692), renal mesangial cells (Takahashi et al. (1995) Biochem. Biophys. Res. Commun. 209: 218–226) and pericytes (Yamagishi et al. (1999) Lab. Invest. 79: 501–509). In monocytes, VEGFR1 is responsible for the VEGF-mediated induction of migration and tissue factor expression (Clauss et al. (1996) J. Biol. Chem., ibid; Barleon et al. (1996) Blood, ibid; Hiratsuka et al. (1998) Proc. Natl. Acad. Sci., ibid). In pericytes, VEGFR1 may mediate the recently described ability of VEGF to act as a mitogen and chemotactic factor (Yamagishi et al. (1999) Lab. Invest., ibid). The role of VEGFR1 in trophoblasts and mesangial cells remains to be elucidated. The expression of VEGFR2 has been detected on hematopoietic stem cells, megakaryocytes/platelets and retinal progenitor cells (Katoh et al. (1995) Cancer Res. 55: 5687–5692; Yang et al. (1996) J. Neurosci. 16: 6089–6099). VEGFR1 and VEGFR2 expression has also been reported on malignant cells including leukemia cells (Katoh et al. (1995) Cancer Res., ibid) and melanoma cells (Gitay-Goren et al. (1993) Biochem. Biophys. Res. Commun. 190: 702–709).

SELEX

A method for the in vitro evolution of nucleic acid molecules with high affinity binding to target molecules has been developed. This method, Systematic Evolution of Ligands by EXponential enrichment, termed SELEX, is described in U.S. patent application Ser. No. 07/536,428, filed Jun. 11, 1990, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, and U.S. patent application Ser. No. 07/931,473, filed Aug. 17, 1992, entitled "Methods for Identifying Nucleic Acid Ligands", now U.S. Pat. No. 5,270,163 (see also WO91/19813), each of which is herein specifically incorporated by reference. Each of these applications, collectively referred to herein as the SELEX Patent Applications, describe a fundamentally novel method for making a nucleic acid ligand to any desired target molecule.

The SELEX method involves selection from a mixture of candidate oligonucleotides and step-wise iterations of binding, partitioning and amplification, using the same general selection theme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield high affinity nucleic acid ligands to the target molecule.

The basic SELEX method may be modified to achieve specific objectives. For example, U.S. patent application Ser. No. 07/960,093, filed Oct. 14, 1992, entitled "Method for Selecting Nucleic Acids on the Basis of Structure", now abandoned, describes the use of SELEX in conjunction with gel electrophoresis to select nucleic acid molecules with specific structural characteristics, such as bent DNA (See U.S. Pat. No. 5,707,796). U.S. patent application Ser. No. 08/123,935, filed Sep. 17, 1993, entitled "Photoselection of Nucleic Acid Ligands", now abandoned, describes a SELEX based method for selecting nucleic acid ligands containing photoreactive groups capable of binding and/or photo-crosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine", now abandoned, describes a method for identifying highly specific nucleic acid ligands able to discriminate between closely related molecules, termed "Counter-SELEX" (See U.S. Pat. No. 5,580,737). U.S. patent application Ser. No. 08/143,564, filed Oct. 25, 1993, entitled "Systematic Evolution of Ligands by EXponential Enrichment: Solution SELEX", now abandoned, (See also U.S. Pat. No. 5,567,588) and U.S. patent application Ser. No. 08/792,075, filed Jan. 31, 1997, entitled "Flow Cell SELEX", now U.S. Pat. No. 5,861,254 describe SELEX-based methods which achieve highly efficient partitioning between oligonucleotides having high and low affinity for a Target molecule. U.S. patent application Ser. No. 07/964,624, filed Oct. 21, 1992, entitled "Nucleic Acid Ligands to HIV-RT and HIV-1 Rev", now U.S. Pat. No. 5,496,938, describes methods for obtaining improved Nucleic Acid Ligands after the SELEX process has been performed. U.S. patent application Ser. No. 08/400,440, filed Mar. 8, 1995, entitled "Systematic Evolution of Ligands by EXponential Enrichment: Chemi-SELEX", now U.S. Pat. No. 5,705,337 describes methods for covalently linking a ligand to its target.

The SELEX method encompasses the identification of high-affinity nucleic acid ligands containing modified nucleotides conferring improved characteristics on the ligand, such as improved in vivo stability or delivery. Examples of such modifications include chemical substitutions at the ribose and/or phosphate and/or base positions. Specific SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides", now abandoned, that describes oligonucleotides containing nucleotide derivatives chemically modified at the 5- and 2'-positions of pyrimidines, as well as specific RNA ligands to thrombin containing 2'-amino modifications (See U.S. Pat. No. 5,660,985). U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement", now abandoned, describes oligonucleotides containing various 2'-modified pyrimidines. PCT/US98/00589, filed Jan. 7, 1998, entitled "Bioconjugation of Oligonucleotides" (WO 98/30720) describes a method for identifying bioconjugates to a target comprising nucleic acid ligands derivatized with a molecular entity exclusively at the 5'-position of the nucleic acid ligands.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX", now U.S. Pat. No. 5,637,459 and U.S. patent application Ser. No. 08/234,997, filed Apr. 28, 1994, entitled "Systematic Evolution of Ligands by Exponential Enrichment: Blended SELEX", now U.S. Pat. No. 5,683,867 respectively. These applications allow the combination of the broad array of shapes and other properties, and the efficient amplification and replication properties, of oligonucleotides with the desirable properties of other molecules. The full text of the above described patent applications, including but not limited to, all definitions and descriptions of the SELEX process, are specifically incorporated herein by reference in their entirety.

BRIEF SUMMARY OF THE INVENTION

The present invention includes methods of identifying and producing nucleic acid ligands to a VEGF receptor and the nucleic acid ligands so identified and produced. A VEGF receptor is any receptor which VEGF binds, including, but not limited to, VEGFR1, VEGFR2, VEGFR3, neuropilin-1. By substantially homologous it is meant a degree of amino acid sequence identity of 70% or more. In particular, RNA sequences are provided that are capable of binding specifically to a VEGF receptor. Also included are oligonucleotides containing nucleotide derivatives modified at the 2' position of the pyrimidines. Specifically included in the invention are the RNA ligand sequences shown in Tables 2 and 3 and FIG. 1 (SEQ ID NOS:2–36). Also included in this invention are RNA ligands of a VEGF receptor that inhibit the function of VEGF signaling.

Further included in this invention is a method of identifying nucleic acid ligands and nucleic acid ligand sequences to a VEGF receptor, comprising the steps of (a) preparing a candidate mixture of nucleic acids, (b) contacting the candidate mixture of nucleic acids with a VEGF receptor, (c) partitioning between members of said candidate mixture on the basis of affinity to a VEGF receptor, and (d) amplifying the selected molecules to yield a mixture of nucleic acids enriched for nucleic acid sequences with a relatively higher affinity for binding to a VEGF receptor.

More specifically, the present invention includes the RNA ligands to a VEGF receptor, identified according to the above-described method, including those ligands shown in Tables 2 and 3 and FIG. 1 (SEQ ID NOS:2–36). Also included are nucleic acid ligands to a VEGF receptor that are substantially homologous to any of the given ligands and that have substantially the same ability to bind a VEGF receptor and inhibit VEGF signaling. Further included in this invention are nucleic acid ligands to a VEGF receptor that have substantially the same structural form as the ligands presented herein and that have substantially the same ability to bind a VEGF receptor and inhibit VEGF signaling.

The present invention also includes other modified nucleotide sequences based on the nucleic acid ligands identified herein and mixtures of the same.

DETAILED DESCRIPTION OF THE INVENTION

Figure 1:
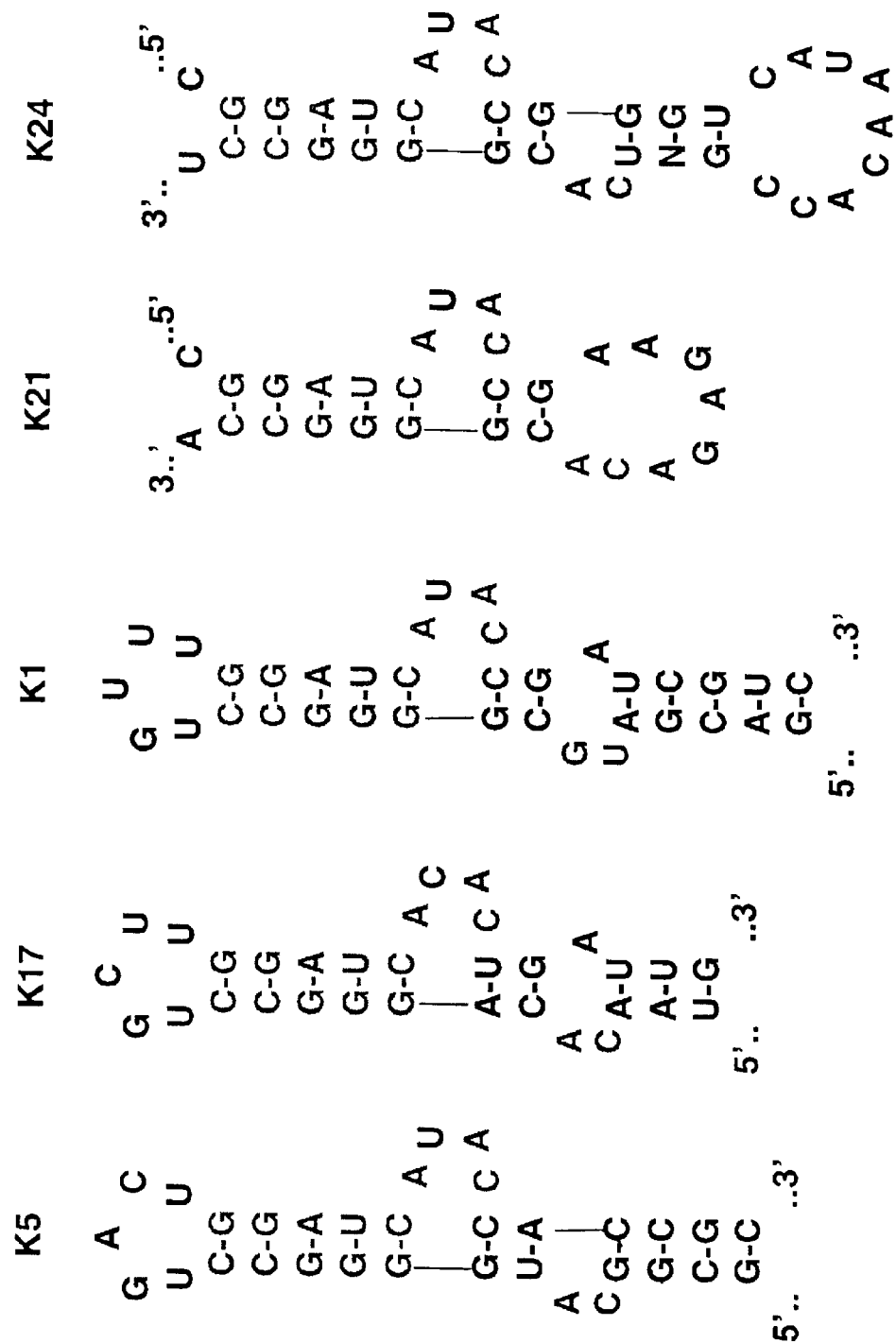
FIG. 1 shows the predicted secondary structures for representative nucleic acid ligands from Table 2.

The central method utilized herein for identifying nucleic acid ligands to a VEGF receptor is called the SELEX process, an acronym for Systematic Evolution of Ligands by EXponential enrichment and involves (a) contacting the candidate mixture of nucleic acids with a VEGF receptor; (b) partitioning between members of said candidate mixture on the basis of affinity to a VEGF receptor; and, (c) amplifying the selected molecules to yield a mixture of nucleic acids enriched for nucleic acid sequences with a relatively higher affinity for binding to a VEGF receptor.

The invention also includes RNA ligands to a VEGF receptor. This invention further includes the specific RNA ligands to a VEGF receptor shown in Tables 2 and 3 and FIG. 1.

SELEX is described in U.S. patent application Ser. No. 07/536,428, entitled "Systematic Evolution of Ligands by EXponential Enrichment", now abandoned, U.S. patent application Ser. No. 07/714,131, filed Jun. 10, 1991, entitled "Nucleic Acid Ligands", now U.S. Pat. No. 5,475,096, and U.S. patent application Ser. No. 07/931,473, filed Aug. 17, 1992, entitled "Methods for Identifying Nucleic Acids Ligands", now U.S. Pat. No. 5,270,163, (see also WO91/19813). These applications, each specifically incorporated herein by reference, are collectively called the SELEX Patent Applications. VEGF nucleic acid ligands have been described in U.S. patent application Ser. No. 08/233,012, filed Apr. 25, 1994, entitled "High Affinity Oligonucleotide Ligands to Vascular Endothelial Growth Factor (VEGF)," now U.S. Pat. No. 5,849,479, U.S. patent application Ser. No. 08/447,169, filed May 19, 1995, entitled "High Affinity Oligonucleotide Ligands to Vascular Endothelial Growth Factor (VEGF)," now U.S. Pat. No. 5,811,533, U.S. patent application Ser. No. 09/156,824, filed Sep. 18, 1998, entitled "High Affinity Oligonucleotide Ligands to Vascular Endothelial Growth Factor (VEGF)," U.S. patent application Ser. No. 08/870,930, filed Jun. 6, 1997, entitled "Vascular Endothelial Growth Factor (VEGF) Nucleic Acid Ligand Complexes," U.S. patent application Ser. No. 08/897,351, filed Jul. 21, 1997, entitled "Vascular Endothelial Growth Factor (VEGF) Nucleic Acid Ligand Complexes," and U.S. patent application Ser. No. 09/254,968, filed Mar. 16, 1999 entitled "Vascular Endothelial Growth Factor (VEGF) Nucleic Acid Ligand Complexes." These applications are each specifically incorporated herein by reference.

Certain terms used to described the invention herein are defined as follows:

"Nucleic Acid Ligand" as used herein is a non-naturally occurring nucleic acid having a desirable action on a target. A nucleic acid ligand is also referred to as an "aptamer" herein. A desirable action includes, but is not limited to, binding of the target, catalytically changing the target, reacting with the target in a way which modifies/alters the target or the functional activity of the target, covalently attaching to the target as in a suicide inhibitor, and facilitating the reaction between the target and another molecule. In the preferred embodiment, the desirable action is specific binding to a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Candidate Mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic. acids or nucleic acids made by a combination of the foregoing techniques. In a preferred embodiment, each nucleic acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups. that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to a VEGF receptor. The SELEX methodology is described in the SELEX Patent Applications.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is a VEGF receptor.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The SELEX method further encompasses combining selected nucleic acid ligands with lipophilic or non-immunogenic, high molecular weight compounds in a diagnostic or therapeutic complex as described in U.S. patent application No. 08/434,465, filed May 4, 1995, entitled "Nucleic Acid Ligand Complexes". VEGF nucleic acid ligands that are associated with a Lipophilic Compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes", now U.S. Pat. No. 5,859,228. VEGF nucleic acid ligands that are associated with a Lipophilic Compound, such as a glycerol lipid, or a non-immunogenic, high molecular weight Compound, such as polyalkylene glycol, are further described in U.S. patent application Ser. No. 08/897,351, filed Jul. 21, 1997, entitled "Vascular Endothelial Growth Factor (VEGF) Nucleic Acid Ligand Complexes". VEGF nucleic acid ligands that are associated with a non-immunogenic, high molecular weight compound or lipophilic compound are also further described in PCT/US 97/18944, filed Oct. 17, 1997, entitled "Vascular Endothelial Growth Factor (VEGF) Nucleic Acid Ligand Complexes" (WO 98/18480). Each of the above described patent applications which describe modifications of the basic SELEX procedure are specifically incorporated by reference herein in their entirety.

In certain embodiments of the present invention it is desirable to provide a complex comprising one or more nucleic acid ligands to a VEGF receptor covalently linked with a non-immunogenic, high molecular weight compound or lipophilic compound. A complex as used herein describes the molecular entity formed by the covalent linking of the nucleic acid ligand of a VEGF receptor to a non-immunogenic, high molecular weight compound. A non-immunogenic, high molecular weight compound is a compound between approximately 100 Da to 1,000,000 Da, more preferably approximately 1000 Da to 500,000 Da, and most preferably approximately 1000 Da to 200,000 Da, that typically does not generate an immunogenic response. For the purposes of this invention, an immunogenic response is one that causes the organism to make antibody proteins. In one preferred embodiment of the invention, the non-immunogenic, high molecular weight compound is a polyalkylene glycol. In the most preferred embodiment, the polyalkylene glycol is polyethylene glycol (PEG). More preferably, the PEG has a molecular weight of about 10–80K. Most preferably, the PEG has a molecular weight of about 20–45K. In certain embodiments of the invention, the non-immunogenic, high molecular weight compound can also be a nucleic acid ligand.

In another embodiment of the invention it is desirable to have a complex comprised of a nucleic acid ligand to a VEGF receptor and a lipophilic compound. Lipophilic compounds are compounds that have the propensity to associate with or partition into lipid and/or other materials or phases with low dielectric constants, including structures that are comprised substantially of lipophilic components. Lipophilic compounds include lipids as well as non-lipid containing compounds that have the propensity to associate with lipid (and/or other materials or phases with low dielectric constants). Cholesterol, phospholipid, and glycerol lipids, such as dialkylglycerol, diacylglycerol, and glycerol amide lipids are further examples of lipophilic compounds. In a preferred embodiment, the lipophilic compound is a glycerol lipid.

The non-immunogenic, high molecular weight compound or lipophilic compound may be covalently bound to a variety of positions on the nucleic acid ligand to a VEGF receptor, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the nucleic acid ligand to VEGF receptor. In embodiments where the lipophilic compound is a glycerol lipid, or the non-immunogenic, high molecular weight compound is polyalkylene glycol or polyethylene glycol, preferably the non-immunogenic, high molecular weight compound is bonded to the 5' or 3' hydroxyl of the phosphate group thereof. In the most preferred embodiment, the lipophilic compound or non-immunogenic, high molecular weight compound is bonded to the 5' hydroxyl of the phosphate group of the nucleic acid ligand. Attachment of the non-immunogenic, high molecular weight compound or lipophilic compound to the nucleic acid ligand of VEGF receptor can be done directly or with the utilization of linkers or spacers.

A linker is a molecular entity that connects two or more molecular entities through covalent bonds or non-covalent interactions, and can allow spatial separation of the molecular entities in a manner that preserves the functional properties of one or more of the molecular entities. A linker can also be known as a spacer.

The complex comprising a nucleic acid ligand to VEGF receptor and a non-immunogenic, high molecular weight compound or lipophilic compound can be further associated with a lipid construct. Lipid constructs are structures containing lipids, phospholipids, or derivatives thereof comprising a variety of different structural arrangements which lipids are known to adopt in aqueous suspension. These structures include, but are not limited to, lipid bilayer vesicles, micelles, liposomes, emulsions, lipid ribbons or sheets, and may be complexed with a variety of drugs and components which are known to be pharmaceutically acceptable. In the preferred embodiment, the lipid construct is a liposome. The preferred liposome is unilamellar and has a relative size less than 200 nm. Common additional components in lipid constructs include cholesterol and alpha-tocopherol, among others. The lipid constructs may be used alone or in any combination which one skilled in the art would appreciate to provide the characteristics desired for a particular application. In addition, the technical aspects of lipid constructs and liposome formation are well known in the art and any of the methods commonly practiced in the field may be used for the present invention.

The SELEX method further comprises identifying bioconjugates to a target. Copending and commonly assigned PCT U.S. patent application No. 98/00589, filed Jan. 7, 1998, entitled "Bioconjugation of Oligonucleotides" (WO 98/30720) describes a method for enzymatically synthesizing bioconjugates comprising RNA derivatized exclusively at the 5'-position with a molecular entity, and a method for identifying bioconjugates to a target comprising nucleic acid ligands derivatized with a molecular entity exclusively at the 5'-position of the nucleic acid ligands. A bioconjugate as used herein refers to any oligonucleotide which has been derivatized with another molecular entity. In the preferred embodiment, the molecular entity is a macromolecule. As used herein, a macromolecule refers to a large organic molecule. Examples of macromolecules include, but are not limited to nucleic acids, oligonucleotides, proteins, peptides, carbohydrates, polysaccharides, glycoproteins, lipophilic compounds, such as cholesterol, phospholipids, diacyl glycerols and dialkyl glycerols, hormones, drugs, non-immunogenic high molecular weight compounds, fluorescent, chemiluminescent and bioluminescent marker compounds, antibodies and biotin, etc. without limitation. In certain embodiments, the molecular entity may provide certain desirable characteristics to the nucleic acid ligand, such as increasing RNA hydrophobicity and enhancing binding, membrane partitioning and/or permeability. Additionally, reporter molecules, such as biotin, fluorescein or peptidyl metal chelates for incorporation of diagnostic radionuclides may be added, thus providing a bioconjugate which may be used as a diagnostic agent.

Certain VEGF receptors (e.g., VEGFR1 and VEGFR2) are strongly upregulated in activated endothelial cells compared to quiescent cells. Activated endothelial cells would be found at areas of inflammation, ischemia reperfusion injury or angiogenesis. Thus, in certain embodiments of the present invention, it is contemplated that VEGF receptor nucleic acid ligands may be used to deliver various chemotherapeutic, radiotherapeutic or imaging entities to such sites.

Thus, the methods described herein and the nucleic acid ligands identified by such methods are useful for both therapeutic and diagnostic purposes. Therapeutic uses include the treatment or prevention of diseases or medical conditions in human patients. Therapeutic uses may also include veterinary applications. The VEGF receptor nucleic acid ligands described herein can be used to treat, inhibit, prevent or diagnose any disease state that involves inappropriate VEGF production, particularly angiogenesis. Angiogenesis rarely occurs in healthy adults, except during the menstrual cycle and wound healing. Angiogenesis is a central feature, however, of various disease states, including, but not limited to cancer, diabetic retinopathy, macular degeneration, psoriasis and rheumatoid arthritis. The present invention, thus, also includes, but is not limited to, methods of treating, inhibiting, preventing or diagnosing diabetic retinopathy, macular degeneration, psoriasis and rheumatoid arthritis. Additionally, VEGF is produced and secreted in varying amounts by virtually all tumor cells. Thus, the present invention, includes methods of treating, inhibiting, preventing, or diagnosing cancer.

Diagnostic utilization may include both in vivo, ex vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art or by the methods described in PCT/US98/00589. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to a VEGF receptor described herein may specifically be used for identification of a VEGF receptor protein.

Labeling markers, such as radionuclides, magnetic compounds, and the like can be conjugated to the VEGF receptor nucleic acid ligand for imaging in an in vivo or ex vivo setting disease conditions in which VEGF receptor is expressed. The marker may be covalently bound to a variety of positions on the VEGF receptor nucleic acid ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the VEGF receptor nucleic acid ligand. In one embodiment, the marker is bonded to the 5' or 3' hydroxyl of the phosphate group thereof. Attachment of the marker can be done directly or with the utilization of a linker.

As discussed above, in other embodiments, the VEGF receptor nucleic acid ligands are useful for the delivery of therapeutic compounds (including, but not limited to, cytotoxic compounds and immune enhancing substances) to tissues or organs expressing VEGF receptor. Conditions in which VEGF receptor may be expressed include, but are not limited to, inflammation, ischemia reperfusion injury and angiogenesis. Those skilled in the art would be able to adapt any VEGF receptor nucleic acid ligand by procedures known in the art to incorporate a therapeutic compound in a complex. The therapeutic compound may be covalently bound to a variety of positions on the VEGF receptor nucleic acid ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the VEGF receptor nucleic acid ligand. In one embodiment, the therapeutic agent can be done directly or with the utilization of a linker.

It is also contemplated that both the marker and therapeutic agent may be associated with the VEGF receptor nucleic acid ligand such that detection of the disease condition and delivery of the therapeutic agent is accomplished together. It is also contemplated that either or both the marker and/or the therapeutic agent may be structure, such as a liposome. As discussed above, methods for conjugating nucleic acid ligands with lipophilic compounds or non-immunogenic compounds in a diagnostic or therapeutic complex are described in U.S. patent application Ser. No. 08/434,465, filed May 4, 1995, entitled "Nucleic Acid Ligand Complexes," which is incorporated herein in its entirety.

Furthermore, VEGFR1 and VEGFR2, for example, belong to a class of tyrosine kinase receptors in which activating phosphorylation and subsequent signaling is initiated by ligand-induced receptor dimerization (Weiss and Schlessinger (1998) Cell 94:277–280). Thus, in certain circumstances, it would be desirable to enhance or control the VEGF signaling. For example, increasing VEGF production may lead to the growth of new blood vessels around a blood clot in heart disease. Surgery may be avoided by having a biochemical alternative. See, for example, Van Velle et al. (1998) Circulation 97:381–90. Thus, the VEGF receptor aptamer can be used as a VEGF substitute. Therefore, it is contemplated that nucleic acid ligands in dimeric or multimeric formulations may reasonably be expected to serve as a receptor agonist, provided that, as would be known to one of skill in the art, the linkage between the aptamers is appropriate to induce productive receptor dimerization.

SELEX provides high affinity ligands of a target molecule. This represents a singular achievement that is unprecedented in the field of nucleic acids research. The present invention applies the SELEX procedure to the specific target of a VEGF receptor. In the Example section below, the experimental parameters used to isolate and identify the nucleic acid ligands to VEGF receptor are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic-acid ligands after SELEX has been performed. The '624 application, entitled "Nucleic Acid Ligands to HIV-RT and HIV-1 Rev", now issued as U.S. Pat. No. 5,496,938, is specifically incorporated herein by reference.

In the present invention, SELEX experiments were performed in order to identify RNA ligands with specific high affinity for a VEGF receptor. This invention includes the specific RNA ligands to a VEGF receptor shown in Tables 2 and 3 and FIG. 1 (SEQ ID NOS: 2–36), identified by the methods described in Example 1. This invention further includes RNA ligands to a VEGF receptor which inhibit VEGF receptor function, presumably by inhibiting binding of VEGF to its receptor or interfering with productive receptor dimerization that is essential for receptor phosphorylation and subsequent signal transduction. The scope of the ligands covered by this invention extends to all nucleic acid ligands of a VEGF receptor, modified and unmodified, identified according to the SELEX procedure. More specifically, this invention includes nucleic acid sequences that are substantially homologous to the ligands shown in Tables 2 and 3 and FIG. 1 (SEQ ID NOS: 2–36). By substantially homologous it is meant a degree of primary sequence homology in excess of 70%, most preferably in excess of 80%, and even more preferably in excess of 90%, 95% or 99%. The percentage of homology as described herein is calculated as the percentage of nucleotides found in the smaller of the two sequences which align with identical nucleotide residues in the sequence being compared when 1 gap in a length of 10 nucleotides may be introduced to assist in that alignment. A review of the sequence homologies of the ligands of a VEGF receptor, shown in Tables 2 and 3 and FIG. 1 (SEQ ID NOS: 2–36) shows that some sequences with little or no primary homology may have substantially the same ability to bind a VEGF receptor. For these reasons, this invention also includes nucleic acid ligands that have substantially the same structure and ability to bind a VEOF receptor as the nucleic acid ligands shown in Tables 2 and 3 and FIG. 1 (SEQ ID NOS: 2–36). Substantially the same ability to bind VEGF receptor means that the affinity is within one or two orders of magnitude of the affinity of the ligands described herein. It is well within the skill of those of ordinary skill in the art to determine whether a given sequence—substantially homologous to those specifically described herein—has substantially the same ability to bind a VEGF receptor.

This invention also includes nucleic acid ligands that have substantially the same postulated structure or structural motifs. Substantially the same structure or structural motifs can be postulated by sequence alignment using the Zuker-fold program (see Zuker (1989) Science 244:48–52). As would be known in the art, other computer programs can be used for predicting secondary structure and structural motifs. Substantially the same structure or structural motif of nucleic acid ligands in solution or as a bound structure can also be postulated using NMR or other techniques as would be known in the art.

One potential problem encountered in the therapeutic, prophylactic, and in vivo diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can be made to increase the in vivo stability of the nucleic acid ligand or to enhance or to mediate the delivery of the nucleic acid ligand. See, e.g., U.S. patent application Ser. No. 08/117,991, filed Sep. 9, 1993, entitled "High Affinity Nucleic Acid Ligands Containing Modified Nucleotides", now abandoned and U.S. patent application Ser. No. 08/434,465, filed May 4, 1995, entitled "Nucleic Acid Ligand Complexes", which are specifically incorporated herein by reference. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the nucleic acid ligands are derived by the SELEX method, the modifications can be pre- or post- SELEX modifications. Pre-SELEX modifications yield nucleic acid ligands with both specificity for their SELEX Target and improved in vivo stability. Post-SELEX modifications made to 2'-OH nucleic acid ligands can result in improved in vivo stability without adversely affecting the binding capacity of the nucleic acid ligand. The preferred modifications of the nucleic acid ligands of the subject invention are 5' and 3' phosphorothioate capping and/or 3'-3' inverted phosphodiester linkage at the 3' end. In one preferred embodiment, the preferred modification of the nucleic acid ligand is a 3'-3' inverted phosphodiester linkage at the 3' end. Additional 2'-fluoro (2'-F) and/or 2'-amino (2'-$NH_2$) and/or 2'-O methyl (2'-OMe) and/or 2'-$OCH_3$ modification of some or all of the nucleotides is preferred. Described herein are nucleic acid ligands that were 2'-F modified and incorporated into the SELEX process. Also described herein are nucleic acid ligands that were 2'-$OCH_3$ modified after the SELEX process was performed.

Other modifications are known to one of ordinary skill in the art. Such modifications may be made post-SELEX (modification of previously identified unmodified ligands) or by incorporation into the SELEX process.

As described above, because of their ability to selectively bind a VEGF receptor, the nucleic acid ligands to a VEGF receptor described herein are useful as pharmaceuticals. This invention, therefore, also includes a method for treating a VEGF receptor-mediated pathological condition by administration of a nucleic acid ligand capable of binding to a VEGF receptor.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Example 1 describes the various materials and experimental procedures used in Examples 2–3. Example 2 describes VEGFR2 affinity selections. Example 3 describes VEGFR1 SELEX.

EXAMPLES

Example 1

VEGFR2 SELEX

Experimental Procedures

VEGFR2 for affinity selections was obtained from R&D Systems (Minneapolis, Minn.). The commercial preparation consists of the extracellular domain of human VEGFR2 (KDR; amino acid residues 1–764; Terman et al. (1992) Biochem. Biophys. Res. Commun. 187:1579–1586) fused to human IgG1 domain (also referred to as the Fc domain). The construct also contains a Factor Xa cleavage site between the KDR and the IgG1 domains and six histidine residues at the carboxy terminus. The protein is a disulfide-linked homodimer expressed in NSO mouse myeloma cell line. For affinity selections, KDR/Fc (50 µg) was digested with Factor Xa (2 µg; New England Biolabs) in 50 mM Tris HCl pH 8.0, 100 mM NaCl, 5 mM $Ca_2Cl_2$ at room temperature for 18 hrs. The Fc fragment was removed by incubation with Protein G-Sepharose for 1 hour at 4° C. Removal of Factor Xa is accomplished by treatment with 50 µl of Xarrest Agarose (Novagen, Madison, Wis.) for 15 min at room temperature. The KDR fragment was verified to be free of the Fc fragment and Factor Xa by SDS-PAGE on 4–12% acrylamide gradient gels and silver staining).

Example 2

VEGFR2 Affinity Selections

The SELEX process has been described in detail in the SELEX Applications. The purified KDR extracellular domain was immobilized on 4.5 µn polystyrene paramagnetic beads (Dynal, Lake Success, N.Y.) by incubating the protein in 1.7 ml microfuge tubes overnight at 4° C. in Hepes-buffered saline supplemented with 1 mM $MgCl_2$ and 1 mM $CaCl_2$ (HBSMC). The beads were then washed three times with 500 µl HBSMC followed by three 500 µl washes with HBSMC containing 0.01% human serum albumin and 0.05% tween 20 (HBSMCHT). Affinity selections were performed by mixing 0.2–50 µl of the bead slurry (0.6% solids w/v) containing about 0.075 µg/ml KDR extracellular domain (based on micro BCA assay) with 50–100 µl of RNA library 40N7 (5'-gggaggacgaugcgg [40N] cagacgacucgcccga-3' (SEQ ID NO: 1)), 2'-fluoropyrimidine RNA) in HBSMCHT (total volume 100 µl) buffer followed by incubation at 37° C. for 30 min and washing with five times with 500 µl HBSMCHT. The beads were then transferred to a new microfuge tube in 500 µl HBSMCHT, the buffer was removed and the beads were resuspended in 20 µl water containing 5 µM 3' primer. Following heating to 95° C. for 5 min and slow cooling to room temperature, 5 µl of 5×reverse transcriptase solution (0.5 M Tris/HCl, pH 9.0 at 21° C. (pH 8.3 at 48° C.), 2.5 M NaCl, 0.5 M Mg(OAc)$_2$, 0.5 M DTT, 5 mM dNTPs, 10 units AMV reverse transcriptase) was added to the tube and the contents were incubated at 48° C. for 30 min. The beads were removed and the remainder of the reverse transcription mixture (25 µl) was added to 75 µl of PCR solution (66.7 mM KCl, 13.3 mM Tris/HCl, pH 8.3, 10 mM $MgCl_2$, 1.33 mM dNTP, 1.33 µM 3' N7 primer, 0.667 µM 5' N7 primer, 0.667 µM 5' primer-FD2, 2.67 µM 5-(and 6-) carboxy-X-rhodamine, 5 units Taq polymerase). Thirty-five cycles of PCR were performed (after the initial heating at 95° C. for 3 min, each cycle consisted of 95° C. for 15 sec, 55° C. for 10 sec, 72° C. for 30 sec). In vitro transcriptions performed by mixing 50 µl of the PCR product with 150 µl of the transcription solution (4 mM 2'-F CTP, 4 mM 2'-F UTP, 1.33 mM ATP, 1.33 mM GTP, 6.67 mM guanosine, 0.267 M Hepes/KOH, pH 8.0, 0.267 M $MgCl_2$, 0.267 M spermidine, 0.267 M DTT, 0.2 units pyrophosphatase, 660 units T7 RNA polymerase) and incubated at 37° C. overnight. The transcripts were purified by gel electrophoresis following a brief DNase treatment to remove the template. The conditions for the six affinity selections performed and the amount of RNA bound at each round is given in Table 1.

Examination of the $K_d$ values of affinity enriched pools from rounds 1–6 (Table 1) reveals that a substantial improvement in affinity occurred already by round 2, with little, if any subsequent improvement in affinity. To address the formal possibility that the aptamers have evolved to the residual Fc domain contaminant in the factor Xa-cleaved preparation, we examined the binding of the random starting pool (round 0) and round 5 pool to KDR/Fc and cMet/Fc. The two Fc-containing constructs were obtained from the same manufacturer (R&D Systems), were expressed in the same cell type (NSO cells) and have identical Fc regions including the six histidines at the carboxy terminus. For KDR/Fc, the $K_d$ values for aptamer pools from rounds 0 and round 5 were 361±16 nM and 0.76±0.22 nM, respectively. The same two pools bound to cMet/Fc with $K_d$ values of 58±9 nM and 74±6 nM. These data suggest that the binding epitope for aptamers in the round 5 pool is the KDR domain, as expected.

Sequences of 30 individual aptamer clones were obtained from the round 5 affinity enriched pool. Most of the sequences (19) could be grouped into a family shown in Table 2 (group A). Clones without obvious sequence similarity to members of family A are shown in Table 3 and are referred to as group B. Predicted secondary structures for representative aptamers from group A are shown in FIG. 1. It is of interest to note that two of the aptamers in group A have circularly permuted primary structures compared to the rest of the aptamers in the group (FIG. 1). This result suggests that the regions outside of the conserved motif shown in FIG. 1 (shading indicates conserved region) are not critical for high affinity binding. We have measured the binding affinity of a subset of aptamers from both groups A and B to KDR/Fc using the nitrocellulose filter binding method. High affinity aptamers were found in both group A and B (Tables 2 and 3).

We next examined whether a group of representative aptamers was able to inhibit the binding of $^{125}$I-VEGF-165 to VEGF receptors expressed on HUVECs. Cells were seeded in 96-well plates at a density of about 10,000 cells/well and maintained until confluent. Culture medium was then replaced with growth factor deficient medium (MEM, 5% heat inactivated fetal bovine serum, 1 µg/ml heparin) for 3–4 hours. Cells were then washed with Dulbecco's phosphate-buffered saline (DPBS) (containing 1 mM $CaCl_2$, 1 mM $MgCl_2$ and 0.1% bovine serum albumin) followed by the addition of 100 µl/well of DPBS. $^{125}$I-VEGF-165 (10 mg/ml) in the presence of varying amounts of aptamers (0.001–1000 nM) was then added to cells for 2 hours at room temperature. Unbound $^{125}$I-VEGF-165 was then removed by washing with DPBS and the cells were lysed with Triton X-100. Lysates were harvested onto glass fiber filters plates and processed for scintillation counting. Aptamers K1, K10, K17 and K21 were tested. Aptamer K1 did not displace $^{125}$I-VEGF-165 at concentrations up to 1000 nM. Aptamers K17 and K21 inhibited $^{125}$I-VEGF-165 receptor binding with $IC_{50}$ values of 163 and 79 nM, respectively. Aptamer K10 was the most potent inhibitor of receptor binding with an $IC_{50}$ of 1 nM. Thus, among the VEGFR2 aptamers tested, both receptor binding antagonists and non-antagonists have been identified.

Example 3
VEGFR1 SELEX

VEGFR1 SELEX was conducted in a similar manner to that described above for VEGFR2. For affinity selections, we used VEGFR1 (Flt-1) extracellular domain fused to the Fc domain. Like KDR/Fc, Flt-1/Fc (R&D Systems, Minneapolis, Minn.) construct also contains a Factor Xa cleavage site between the Flt-1 and the IgG1 domains and six histidine residues at the carboxy terminus. The protein is a disulfide-linked homodimer expressed in NSO mouse myeloma cell line.

Examination of the $K_d$ values of affinity enriched pools from rounds 0 and 5 (Table 4) reveals that a only a modest improvement in affinity occurred already by round 5. This is probably due to the very high affinity of the extracellular domain of VEGFR1 for nucleic acids, as reflected by the $K_d$ value of 0.20±0.05 nM.

TABLE 1

SELEX results for rounds 1–6. The number of molecules bound was determined by quantitative PCR. Nitrocellulose filter binding was used to determine the $K_d$ for each of the pools using $^{32}P$ end-labeled transcripts and KDR/Fc dimer (in HBSMC buffer at 37° C.). The affinity of the unselected randomized starting library is 36 ± 3 nM.

| Round | Bead volume, µl | [RNA], µM | Molecules RNA bound to KDR beads | Molecules RNA bound to empty beads | Signal/ noise | $K_d$ pool, nM |
|---|---|---|---|---|---|---|
| 1 | 50 | 5 | $3.2 \times 10^9$ | $1.0 \times 10^9$ | 3.2 | Not determined |
| 2 | 50 | 2 | $1.8 \times 10^{10}$ | $4.9 \times 10^7$ | 367 | 0.68 ± 0.14 |
| 3 | 10 | 6.1 | $3.3 \times 10^{10}$ | $2.1 \times 10^8$ | 157 | 0.80 ± 0.16 |
| 4 | 2 | 2.5 | $9.4 \times 10^9$ | $5.5 \times 10^7$ | 171 | 0.581 ± 0.08 |
| 5 | 0.4 | 5 | $8.5 \times 10^8$ | $3.8 \times 10^7$ | 22 | 0.83 ± 0.12 |
| 6 | 0.2 | 2.5 | $2.0 \times 10^8$ | $5.2 \times 10^7$ | 3.8 | 0.44 ± 0.05 |

TABLE 2

Aligned sequences a family of VEGFR2 aptamers. Nucleotides from the fixed and initially randomized regions are shown in lowercase and uppercase letters, respectively. Highly conserved nucleotides are shown in boldface letters. Regions predicted to be base-paired are underlined. The last two sequences in the set are circularly permuted and are split between two lines (with equality sign) to allow alignment with the other sequences. $K_d$ values for a subset of aptamers tested for binding to KDR/Fc are shown.

| clone | SEQ ID NO. | Sequence | $K_d$, nM |
|---|---|---|---|
| K3 | 2 | ggagggacgaugcggCAUGGGGCCUGACU-GGAUCAUACCACGGGCUUUCUGGUcagagacucgcccga | 0.51 ± 0.14 |
| K5 | 3 | ggagggacgaugcggACU-GGAUCAUACCACCGGCUUCCUCUGGUcagacgacucgcccga | 0.44 ± 0.07 |
| K102 (n = 2) | 4 | ggagggacgaugcggCAUGGGGCCUGACU-GGAUCAUACCACCGGCUUCCUCUGGUcagacgacucgcccga | |
| K119 | 5 | ggagggacgaugcggCCUGGGGCCUGACU-GGAUCAUACCACCGGCUUCCUCUGGUcagacgacucgcccga | |
| K7 | 6 | ggagggacgaugcggAC-GAUAACACAGGGCCUGCUU-GGAUCACACUGAUUGCGCCcagacgacucgcccga | 0.46 ± 0.02 |
| K17 | 7 | ggagggacgaugcggACANAUAAACACAGGGCCUGCUU-GGAUCACACUGAUUGCGCCcagacgacucgcccga | 0.24 ± 0.08 |
| K124 | 8 | ggagggacgaugcggCCGAUAACACAGGGCCUGCUU-GGAUCACACUGAUUGCGCCcagacgacucgcccga | |
| K103 (n = 3) | 9 | ggagggacgaugcggACCGAUAACACAGGGCCUGCUU-GGAUCACACUGAUUGCGCCcagacgacucgcccga | |
| K1 | 10 | ggagggacgaugcggGGCCUGUUU-GGAUCAUACCGAUCCAACAGUGGUcagagcgacuc.. | 0.07 ± 0.01 |
| K2 (n = 4) | 11 | ggagggacgaugcggGGCCUGUUU-GGAUCAUACCGAUCUCAAUCCUAAAGUGGUcagacgacucgcccga.. | 0.27 ± 0.03 |
| K101 (n = 7) | 12 | ggagggacgaugcggGGCCUGCUU-GGAUCAUACCGAUCUCAAUCCUAAAGUGGUcagacgacucgcccga | |
| K115 (n = 2) | 13 | ggagggacgaugcggGGCCUGCUU-GGAUCAUACCGAUCUCAAGCCUAAGUGGUcagacgacucgcccga | |
| K118 (n = 3) | 14 | ggagggacgaugcggUCUGAAGAGUAAGGGGCCUGUC-GGAUCACACCUGCCGUcagacgacucgcccga | |
| K136 | 15 | ggagggacgaugcggAGGGGCCUAUUC-GGAUCAUACCUCGCAGUUCCUUUUACCCCGUcagacgacucgcccga | |
| K121 | 16 | ggagggacgaugcggAGGGGCCUAUUC-GGAUCAUACUCGCAGUUCCUUACCCCGUcagacgacucgcccga | |
| K127 | 17 | ggagggacgaugcggGGGGCCUAUAACUUGGAUCAU-CAGCACCUGCCACCACCCUcagacgacucgcccga | |
| K110 | 18 | ggagggacgaugcggAGUGCCUUUGGAACUU-CGUAUUUGUCUGCUCCCGGUcagacgacucgcccga | |
| K21 | 19 | 5'ggagggacgaugcggAUCAUACCGAAGAGA =<br>= CACGGGGCACCAUAUCCUCACCCCcagacgacucgcccga3' | 0.26 ± 0.05 |
| K24 | 20 | 5'ggagggacgaugcggAUCAUACCGGGUCAUA =<br>= ACACCGNUCACGGGGCCCUUNCCGUcagacgacucgcccga3' | 0.97 ± 0.08 |

TABLE 3

Ungrouped sequences of VEGFR2 aptamers showing only the initially randomized region. $K_d$ values for a subset of aptamers tested for binding to KDR/Fc are shown.

| Clone | SEQ ID NOS. | Sequence | $K_d$, nM |
|---|---|---|---|
| K4 | 21 | AGGUGCUCCUUUGGAACUUCGUAUUUGUCUCCUCCUGGU | 0.28 ± 0.04 |
| K10 | 22 | UUGAUCGAGGUUCUAAGGCCUAUUUCCUGACUUUCUCCCC | 0.47 ± 0.25 |
| K11 (n = 4) | 23 | UUGAUCGAGGUUCUAAAGCCUAUUUCCUGACUUUCUCCCC | 0.61 ± 0.13 |
| K12 | 24 | AAACGGAAGAAUUGGAGACCGACGUCGACCUCUUGGCCC | 15.4 ± 2 |
| K108 | 25 | UUGAUCGAGGUUCUAAAGCCUAUUUCUGACUUUCUCCCC | |
| K109 (n = 4) | 26 | ACGAUGCGGAAUCAGUGAAUGCUUAUAGCUCCGCCUGGU | |
| K111 | 27 | AAGCCGCCAGAAUUGGAACAACCCCUUUCGCACGCUCCCC | |
| K116 | 28 | CGAAACGGAAUACUUGGAUACACCGCACUUCCCGACCCCU | |
| K6 | 29 | AGCACUUGACCCACNACCAGAAAGCCAGCC | 0.98 ± 0.05 |
| K13 | 30 | AACCAAUUAAGUCUGGCAAAUCUCUCUGUG | 0.75 ± 0.09 |
| K23 | 31 | ACACACACAUCAUAAACAUUGUCCGUUGAC | 2.2 ± 0.2 |

TABLE 4

SELEX results for rounds 1–6. The number of molecules bound was determined by quantitative PCR. Nitrocellulose filter binding was used to determine the $K_d$ for each of the pools using $^{32}$P end-labeled transcripts and Flt-1/Fc dimer (in HBSMC buffer at 37° C.). The affinity of the unselected randomized starting library is 0.20 ± 0.05 nM. ND = not determined.

| Round | Bead volume, μl | [RNA], μM | Molecules RNA bound to KDR beads | Molecules RNA bound to empty beads | Signal/ noise | $K_d$ pool, nM |
|---|---|---|---|---|---|---|
| 1 | 50 | 2.7 | 2.6 × 10$^{10}$ | 1.5 × 10$^8$ | 173 | ND |
| 2 | 25 | 2 | 2.1 × 10$^{12}$ | 1.2 × 10$^8$ | 17500 | ND |
| 3 | 2.5 | 1.5 | 3.6 × 10$^{11}$ | 7.2 × 10$^7$ | 5000 | ND |
| 4 | 0.25 | 1.5 | 6.2 × 10$^{10}$ | 8.6 × 10$^7$ | 721 | ND |
| 5 | 0.025 | 1.5 | 1.1 × 10$^{10}$ | 8 × 10$^6$ | 1375 | 0.093 ± 0.037 |

We claim:

1. A purified and isolated non-naturally occurring RNA nucleic acid ligand to VEGFR2 wherein said ligand is selected from the group consisting of the sequences set forth in SEQ ID NO:2 to SEQ ID NO:36.

* * * * *